United States Patent [19]

Sacks et al.

[11] Patent Number: 5,281,256
[45] Date of Patent: Jan. 25, 1994

[54] GAS CHROMATOGRAPHY SYSTEM WITH COLUMN BIFURCATION AND TUNABLE SELECTIVITY

[75] Inventors: Richard D. Sacks; Michael L. Akard, both of Ann Arbor, Mich.

[73] Assignee: Regents of the University of Michigan, Ann Arbor, Mich.

[21] Appl. No.: 975,289

[22] Filed: Nov. 12, 1992

Related U.S. Application Data

[63] Continuation-in-part of Ser. No. 590,174, Sep. 28, 1990, Pat. No. 5,096,471, Ser. No. 817,306, Jan. 6, 1992, Pat. No. 5,205,845, and Ser. No. 710,703, Jun. 5, 1991, Pat. No. 5,141,532.

[51] Int. Cl.$^5$ .............................................. B01D 15/08
[52] U.S. Cl. ........................................ 95/86; 96/102; 96/104
[58] Field of Search ................... 55/67, 197, 386; 73/23.35, 23.36, 23.39, 23.42

[56] References Cited

U.S. PATENT DOCUMENTS

| | | | |
|---|---|---|---|
| 2,757,541 | 8/1956 | Watson et al. | 73/422 |
| 2,972,246 | 2/1961 | Reinecke et al. | 73/23 |
| 2,981,092 | 4/1961 | Marks | 55/67 X |
| 3,000,218 | 9/1961 | Marks et al. | 73/422 |
| 3,111,835 | 11/1963 | Jenkins | 73/23 |
| 3,119,251 | 1/1964 | Bowers | 73/23 |
| 3,136,616 | 6/1964 | Thompson | 55/67 |
| 3,201,922 | 8/1965 | Villalobos | 55/67 |
| 3,201,971 | 8/1965 | Villalobos | 73/23.1 |
| 3,220,164 | 11/1965 | Golay | 55/67 |
| 3,223,123 | 12/1965 | Young | 55/67 X |
| 3,225,520 | 12/1965 | Burow | 55/67 |
| 3,236,603 | 2/1966 | Durrett et al. | 55/197 X |
| 3,386,279 | 6/1968 | Sternberg | 73/23.1 |
| 3,422,665 | 1/1969 | Haase | 55/386 X |
| 3,425,807 | 2/1969 | Levy | 55/67 X |
| 3,444,722 | 5/1969 | Roof | 73/23.1 |
| 3,458,437 | 7/1969 | Ouano | 55/386 X |
| 3,477,207 | 11/1969 | Auger | 55/197 |
| 3,496,702 | 2/1970 | Carel et al. | 55/67 |
| 3,514,262 | 5/1970 | Ayers et al. | 55/386 X |
| 3,524,305 | 8/1970 | Ives | 55/386 |
| 3,537,297 | 11/1970 | Loyd et al. | 73/23.1 |
| 3,550,428 | 12/1970 | Mator et al. | 73/23.1 |
| 3,585,002 | 6/1971 | Boys | 55/197 X |
| 3,628,872 | 12/1971 | Miranda | 356/201 |
| 3,630,371 | 12/1971 | Hrdina | 55/67 X |
| 3,676,649 | 7/1972 | Burk | 73/23.1 X |
| 3,735,565 | 5/1973 | Gilby et al. | 55/197 |
| 3,798,973 | 3/1974 | Estey | 73/23.1 X |
| 3,807,217 | 4/1974 | Wilkins et al. | 55/386 X |
| 3,887,345 | 6/1975 | Pollock et al. | 55/386 |
| 3,948,602 | 4/1976 | Solomon | 55/67 X |
| 4,001,112 | 1/1977 | Barker et al. | 55/67 X |

(List continued on next page.)

OTHER PUBLICATIONS

Scientific American by Walker-1986, pp. 118-124.
"Electrically Heated Cold Trap Inlet System for High--Speed Gas Chromatography"-Ewels et al.-1985, Anal. Chem. 57, 2774-2779.
"Evaluation of a Nitrogen-Cooled, Electrically Heated Cold Trap Inlet for High-Speed Gas Chromatography"-Mouradian et al.-1990, J. Chrom. Sci. vol. 28, 643-648.
"Fast-GC for Industrial Hygiene Monitoring Analysis'-'-Levine et al. 1985.
"Electrically Heated Cold Trap Inlet System for Com- (List continued on next page.)

*Primary Examiner*—Robert Spitzer
*Attorney, Agent, or Firm*—Harness, Dickey & Pierce

[57] ABSTRACT

A gas chromatography system featuring column bifurcation and pressure tuning. The system of this invention incorporates a bifurcated system in which samples eluting from a first separation column are directed selectively through one of two or more additional separation columns. Flow directing is achieved through the use of valves which switch carrier gas which are outside of the path of the analyte mixture. Effective tuning of the system is provided by adjusting the intermediate pressure which controls the effective lengths of the initial separation column and the additional final separation columns.

15 Claims, 6 Drawing Sheets

U.S. PATENT DOCUMENTS

| | | |
|---|---|---|
| 4,035,168 | 7/1977 | Jennings ............................... 55/67 |
| 4,038,053 | 7/1977 | Golay ................................... 55/160 |
| 4,126,396 | 11/1978 | Hartmann et al. ................. 356/434 |
| 4,192,614 | 3/1980 | deMey, II et al. ................. 356/410 |
| 4,199,260 | 4/1980 | Kusnetz et al. ..................... 356/411 |
| 4,204,952 | 5/1980 | Snyder ............................... 55/67 X |
| 4,271,697 | 6/1981 | Mowery, Jr. ....................... 73/61.1 C |
| 4,274,967 | 6/1981 | Snyder ............................... 55/67 X |
| 4,432,649 | 2/1984 | Krause ............................... 356/438 |
| 4,468,124 | 8/1984 | Berick ............................... 356/411 |
| 4,470,832 | 9/1984 | Sugawara et al. ................. 55/197 |
| 4,475,813 | 10/1984 | Munk ............................... 356/73 |
| 4,477,266 | 10/1984 | Yang et al. ......................... 55/67 |
| 4,536,199 | 8/1985 | Toon ................................... 55/67 |
| 4,617,032 | 10/1986 | Wells ................................... 55/67 |
| 4,805,441 | 2/1989 | Sides et al. ......................... 55/67 X |
| 4,861,358 | 8/1989 | Mueller et al. ..................... 55/386 |
| 4,863,871 | 9/1989 | Munari et al. ..................... 436/161 |
| 4,923,486 | 5/1990 | Rubey ............................... 55/67 |
| 4,932,272 | 6/1990 | Hogg ............................... 73/864.83 |
| 4,962,042 | 10/1990 | Morabito et al. ................... 55/67 X |
| 5,028,243 | 7/1991 | Rubey ............................... 55/67 |
| 5,096,471 | 3/1992 | Sacks et al. ....................... 55/67 |
| 5,141,532 | 8/1992 | Sacks et al. ....................... 55/386 X |

OTHER PUBLICATIONS puter-Controlled High-Speed Gas Chromatography'-'-Lanning et al.-1988, Anal. Chem., 60, 1994-1996.

"Large Volume Sample Introduction into Narrow Bore Gas Chromatography Columns using Thermal Desorption Modulation and Signal Averaging"-Liu et al.-1989.

"Liquid Chromatography Absorbance Detector With Retroreflective Array for Aberration Compensation and Double Pass Operation"-Pang et al.-1985, Anal. Chem.

"Measurements of Organic Vapors at Sub-TLV Concentrations Using Fast Gas Chromatography'-'-Mouradian et al.-1990, Am. Ind. Hyg. Assoc. J. 51(2):90-95.

"Rapid Evaporation of Condensed Gas Chromatographic Fractions" Hopkins et al.-1978, J. of Chrom., 158, 465-469.

"Sample Enrichment in High Speed Narrow Bore Capillary Gas Chromatography"-VanEs et al.-1988, J. High Resolution Chrom. & Chrom. Com., 852-857.

"Simultaneous Analysis of Methane and Non-Methane Hydrocarbons in Air Using Gas Chromatography/Frame Ionization Detection With a Solid Sorbent Sample Interference"-Zweidinger et al.-1990.

"Theoretical Aspects and Practical Potentials of Rapid Gas Analysis in Capillary Gas Chromatography'-'-Tijssen et al.-1987, Anal. Chem., 59, 1007-1015.

GAS CHROMATOGRAPHY SYSTEM WITH COLUMN BIFURCATION AND TUNABLE SELECTIVITY

CROSS REFERENCE TO RELATED APPLICATION

This application is a continuation-in-part of the following applications: Ser. No. 590,174, filed on Sep. 28, 1990, issued as U.S. Pat. No. 5,096,471; Ser. No. 817,306, filed on Jan. 6, 1992, issued as U.S. Pat. No. 5,205,845 and Ser. No. 710,703, filed on Jun. 5, 1991 issued as U.S. Pat. No. 5,141,532, the disclosures of which are hereby incorporated by reference.

BACKGROUND AND SUMMARY OF THE INVENTION

This invention relates to a high speed gas chromatography system and particularly to such systems employing column bifurcation and tunable selectivity for improved rapid separation of components of an analyte mixture.

Gas chromatography is unsurpassed in its selectivity, sensitivity, and cost effectiveness. It is applicable for at least several hundred thousand compounds of low to moderate boiling point, including compounds in the $C_1$ to $C_5$ range. The process is also unique in its ability to obtain complete speciation of complex mixtures of compounds.

In gas chromatography analysis the analyte mixture is separated into its components by eluting them from a column having a sorbent by means of a moving gas. In gas-liquid chromatography, which is a type in widespread use at present, the column comprises a nonvolatile liquid or solid sorbent coated as a thin layer on an inner support structure, generally the inside surface of a capillary tube. The moving gas phase, called the carrier gas, flows through the chromatography column. The analyte partitions itself between the moving gas phase and the sorbent and moves through the column at a rate dependent upon the partition coefficients or solubilities of the analyte components. The analyte is introduced at the entrance end of the column within the moving carrier gas stream. The components making up the analyte become separated along the column and elute at intervals characteristic of the properties of the analyte components. A detector, for example, a thermal conductivity detector or a flame ionization detector (FID) at the exit end of the analytical column responds to the presence of the analyte components. Upon combustion of the eluted components at the FID, charged species are formed in the flame. The flame characteristics are monitored through a biased ion detector which, along with associated signal processing equipment, produces a chromatogram which is a time versus detector signal output curve. The trace for complex mixtures includes numerous peaks of varying intensity. Since individual constituents of the analyte produce peaks at characteristic times and whose magnitude is a function of their concentration, much information is gained through an evaluation of a chromatogram.

While gas chromatography systems presently available perform satisfactorily, designers of such systems are continually attempting to optimize the capabilities of this separation procedure. Of particular interest is providing high speed gas chromatography which is advantageous in providing process stream control in industrial applications and in monitoring transient processes, for example, internal combustion engine exhaust gas compositions. The use of special inlet systems when combined with relatively short separation columns operated at unusually high carrier gas flow rates, has allowed separation of relatively simple mixtures on a time scale of a few seconds. However, some samples require much longer separation times because of the probability of co-eluting components. This probability is the result of the inevitable decrease in resolution when separation times are drastically reduced. To make high speed separation more practical, and to be able to apply fast gas chromatography techniques to a wider range of potential applications, it is necessary to enable adjustment of the selectivity of the system for specific sets of target compounds.

In view of the foregoing, an objective of this invention is to improve the selectivity of high speed chromatography by using high speed column bifurcation switching and pressure tuning techniques. Certain groups of components in a mixture which are not separated on an initial pre-separation column are switched to one or more columns which may have a different stationary phase where they are separated. High speed precision switching is achieved using this invention without the use of valves in the sample flow path. The pressure at the switching point is adjustable in accordance with this invention to improve the selectivity of the separation. By changing this pressure, the influence of the various columns on the separation process is changed. This can result in the shifting of overlapping peaks in such a way that they no longer overlap.

Preferably, in accordance with this invention, column switching is achieved through the use of a computer control system. Through such precision column switching and pressure tuning techniques, the selective transfer of components to an appropriate column can be provided which will optimize their separation and will thus allow a more efficient utilization of the available separating power of short columns operated at high carrier gas flow rates. The systems in accordance with this invention provide for the selectivity tuning of a tandem column combination to provide adjustments of the times at which components are eluted to ensure lack of overlapping or co-eluting components.

Additional benefits and advantages of the present invention will become apparent to those skilled in the art to which this invention relates from the subsequent description of the preferred embodiments and the appended claims, taken in conjunction with the accompanying drawings.

DETAILED DESCRIPTION OF THE INVENTION

Figure 1:
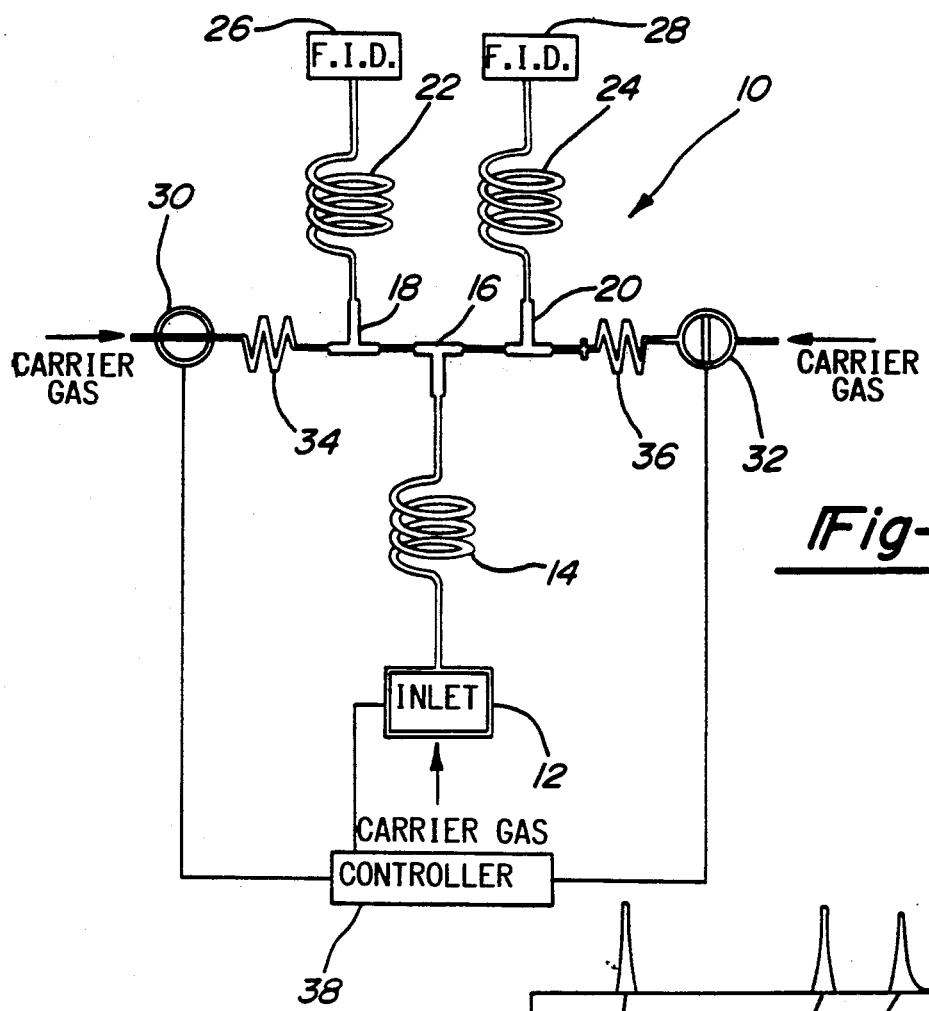
FIG. 1 is a pictorial view of a gas chromatography system in accordance with the first embodiment of this invention.

A gas chromatography (GC) system in accordance with a first embodiment of this invention is shown in schematic fashion in FIG. 1 where it is generally designated by reference number 10. As shown, GC system 10 incorporates an inlet system designated by reference number 12 which is intended to input a narrow band sample "plug" into gas chromatography separation column 14 entrained in a stream of carrier gas. Various configurations of inlet system 12 can be provided. For example, mechanical injection valves can be incorporated as described in related patent application Ser. No. 817,306. Alternatively, cryofocusing system based on cold-trapping such as described in U.S. Pat. No. 5,141,532 and application Ser. No. 717,356, could be incorporated. Separation column 14 can also take various forms including columns having various types of liquid stationary phase materials. In addition, solid stationary phase-type columns using absorbent materials such as what is commonly known as porous layer open tubular (PLOT) columns, liquid crystal columns or columns having polar or non-polar stationary phases could also be used. In the described example of this invention, however, it will be initially assumed that column 14 uses a nonpolar liquid stationary phase material.

Column 14 is connected to a branching connection in the form of Tee-fitting 16 where the flow is split an directed into separate branches each having additional branching connectors in the form of Tee-fittings 18 and 20. The outlets of Tee-fittings 18 and 20 are connected to chromatography separation columns 22 and 24, respectively. Like column 14, the configurations of columns 22 and 24 can be selected from various column types including those mentioned above. However, in the first example of this invention which will be described, it is assumed that column 22 has a polar stationary phase coating whereas column 24 has a non-polar stationary phase coating which is identical to that of column 14 such that columns 24 and 14 have equivalent selectivities.

Analyte components eluted from columns 22 and 24 are, in the embodiment shown, directed to separate and distinct detectors shown as flame ionization detectors (FIDs) 26 and 28. Alternatively, the functions of FIDs 26 and 28 could be provided through the use of a single FID. However, in the examples of implementation of GC system 10 which will be described, it is assumed that separate detectors are employed.

Into each of the Tee-fittings 18 and 20, there is provided a controllable source of carrier gas provided by connecting a source of carrier gas through on/off gas valves 30 and 32, and capillary pneumatic restrictors 34 and 36. Capillary restrictors 34 and 36 are simply lengths of small diameter capillary tubing which are used to balance flow conditions and provide carrier gas at a desired pressure as will be described in more detail. Valves 30 and 32 are operated by controller 38 which both coordinates the injection of a sample by inlet 12 and the opening and closing of valves 30 and 32 for column bifurcation, as will be described in more detail. Tee-fittings 16, 18 and 20, valves 30 and 32, and restrictors 34 and 36, along with the associated connecting conduits comprise a sample switching network which enables precise control of the flow path of sample components eluting from column 14 into columns 22 and 24.

Assuming that injection of an analyte mixture has occurred, the mixture becomes at least partially separated as the components partition themselves between the carrier gas flow and stationary phase material of the pre-separation column 14. In FIG. 1, valve 30 is shown open and valve 32 is shown closed. In this configuration, components eluting from column 14 are driven by carrier gas flow through valve 30 and restrictor 34, transferring the sample components into column 24. An additional carrier gas flow without sample components from valve 30 occurs through column 22 which continues the separation process for any components which were previously switched into that column. Thus, by selectively opening and closing valves 30 and 32, the materials eluted from column 14, and entering Tee-fitting 16 can be selectively directed either to column 22 or column 24. If carrier gas is supplied at the same pressure at inlet 12 and valves 30 and 32, restrictors 34 and 36 provide a pressure drop to produce a pressure differential for driving carrier gas and analyte through column 14. Flow through columns 22 and 24 occurs since FIDs 26 and 28 vent to atmosphere. Alternatively, however, FID's 26 and 28 could vent at another pressure, for example, subatmospheric. The various pressures applied to the system would be chosen to ensure carrier gas flow in the desired direction through the various columns.

It should be noted that valves 30 and 32 are located outside of the sample flow path, thus minimizing dead volumes and eliminating sample contamination which can occur on valve surfaces. Preferably, conduits making up the system are deactivated glass or fused silica material, as are fittings 16, 18 and 20 and restrictors 34 and 36. Accordingly, the sample components only come in contact with surfaces which do not contaminate the sample and the separation columns.

Figure 2:
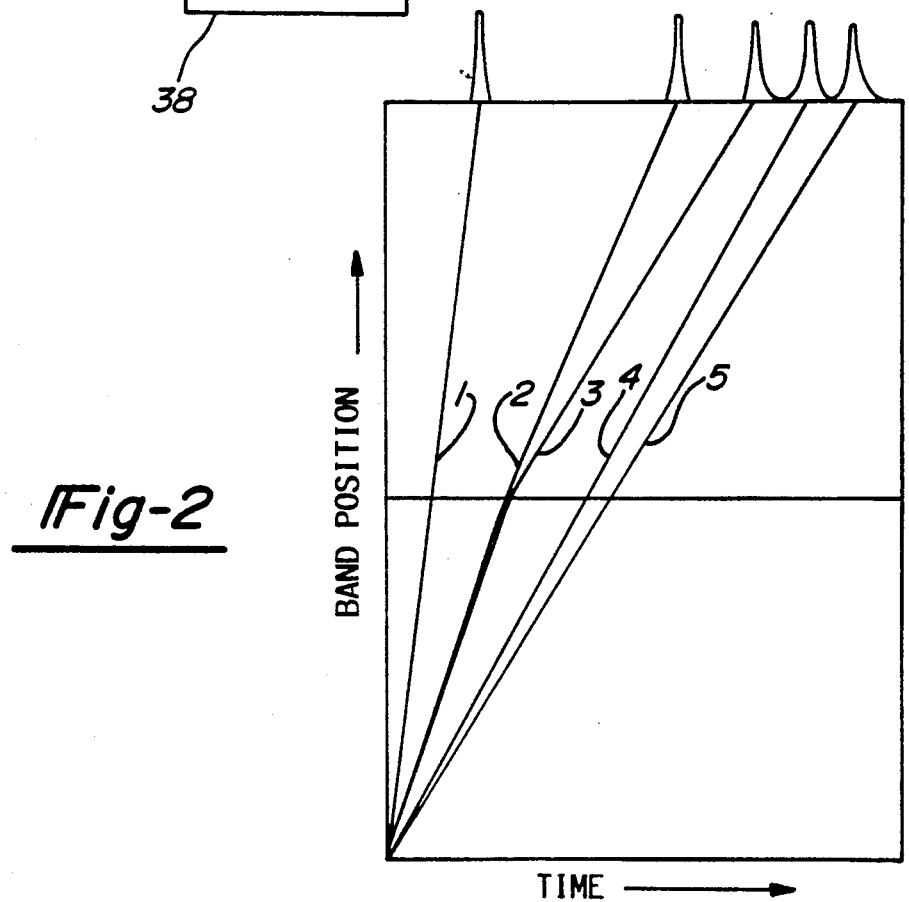
FIG. 2 is a graph of the position of components of an illustrative analyte mixture on the columns of FIG. 1 with respect to time.

Now with reference to FIG. 2, the progress of five components of a hypothetical analyte mixture through gas chromatography system 10 will be described. In the figure, the position of the components which are arbitrarily numbered 1 through 5 are shown on the Y axis, versus time on the X axis. The bottom of the figure represents injection, the solid horizontal line in the center of the figure corresponds to the location of the switching network and the top designates elution at an FID. Therefore, the bottom half of the figures represents flow through column 14 whereas the top half represents flow through one of columns 22 or 24. It should be recognized that the progress lines of the components shown in FIG. 2 are a simplification for purposes of illustration since in actual gas chromatography separation, the carrier gas undergoes compression and the traces are curved rather than straight lines. The slope of the lines in FIG. 2 represent the velocity of the components passing through the respective elements of GC system 10. Through column 14, the components move at different velocities with the exception of components 2 and 3 which are not differentially separated through column 14. GC system 10 is, however, operated such that at the time component 1 enters the switching network, it continues to flow through column 24, which as mentioned previously, has the same selectivity as that of column 14 (the velocity may, however, change due to carrier gas flow rate or other factors). However, when the plugs of materials 2 and 3 enter the switching network, valve 32 is opened and valve 30 is closed to direct those components into column 22 which is capable of separating those components. The flow direction is again changed by opening valve 30 and closing valve 32 creating a pressure differential which changes sample flow direction so that components 4 and 5 flow through column 24.

It should be noted that due to the different selectivity of column 22 with respect to components 2 and 3, those components exhibit a different slope and are thus being separated on column 22. The result is a chromatogram as shown at the top of the figure where each component exhibits separate and distinct peaks which is essential for quantitative analysis. Without use of the switching networks, components 2 and 3 would co-elute, precluding quantitative evaluation of those components.

Additional examples of implementation of GC system 10 will be described based on the separation of an actual complex mixture containing the components having characteristics as described in the following table. The table also provides designating letters which will be used to identify the compounds in representative chromatograms shown in additional Figures.

| SAMPLE MIXTURE COMPONENTS | | |
| --- | --- | --- |
| Peak | Compound | Boiling Point, °C. |
| A | Propionaldehyde | 47–49 |
| B | n-Hexane | 68–69 |
| C | 1-Bromopropane | 71 |
| D | Chloroform | 60–61 |
| E | n-Heptane | 98 |
| F | Valeraldehyde | 100–103 |
| G | Isobutyl alcohol | 108 |
| H | 4-Methyl,2-pentanone | 117–118 |
| I | 1-Butanol | 117 |
| J | n-Octane | 125–127 |
| K | Dibromomethane | 96–98 |
| L | 2-Fluorotoluene | 113–114 |
| M | Butyl Acetate | 124–126 |
| N | Chlorobenzene | 132 |
| O | n-Nonane | 151 |

Figure 3:
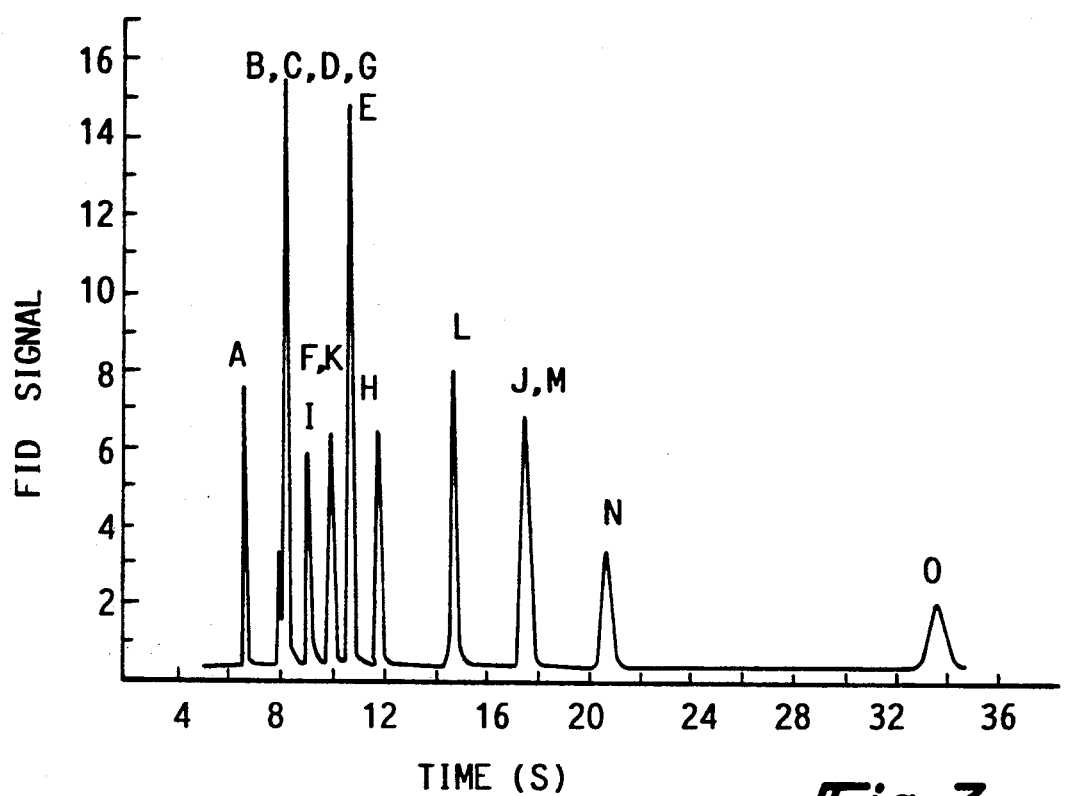
FIG. 3 is a representative chromatogram of components eluting from a first tandem column combination from the system shown in FIG. 1 without column switching.
Figure 4:
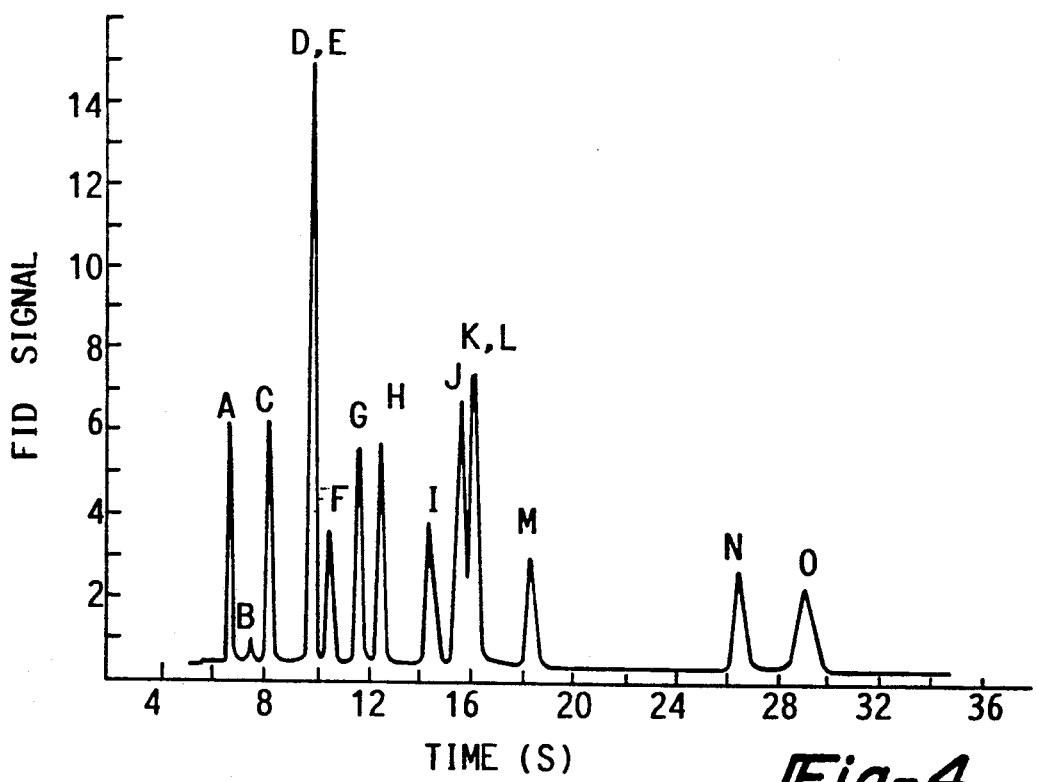
FIG. 4 is a representative chromatogram of components eluting from a second tandem column combination from the system shown in FIG. 1 without column switching.

FIGS. 3 and 4 show high speed chromatograms using GC system 10 in conjunction with a high speed cryofocusing inlet system. As indicated by the above table, the analyte mixture contains fifteen components labeled A through O. The components and their boiling points are listed. FIG. 3 is a chromatogram of all components of the mixture passing through columns 14 and 24 without switching. As indicated, components B, C, D and G co-elute, as do compounds F and K, and J and M. Due to this co-elution, individual peaks resulting from each individual component is not provided and thus quantitative analysis of these co-eluting components is not possible. FIG. 4 is a chromatogram obtained by directing all the components from column 14 to column 22, again without switching as the components elute from column 14. In this instance, compounds D and E co-elute as do K and L. It is also noted that compound J is not adequately separated from the K-L pair. Thus it is shown that neither tandem columns pair 14 and 22, or 14 and 24 provide adequate separation of all components of the mixture under these conditions.

Figure 5:
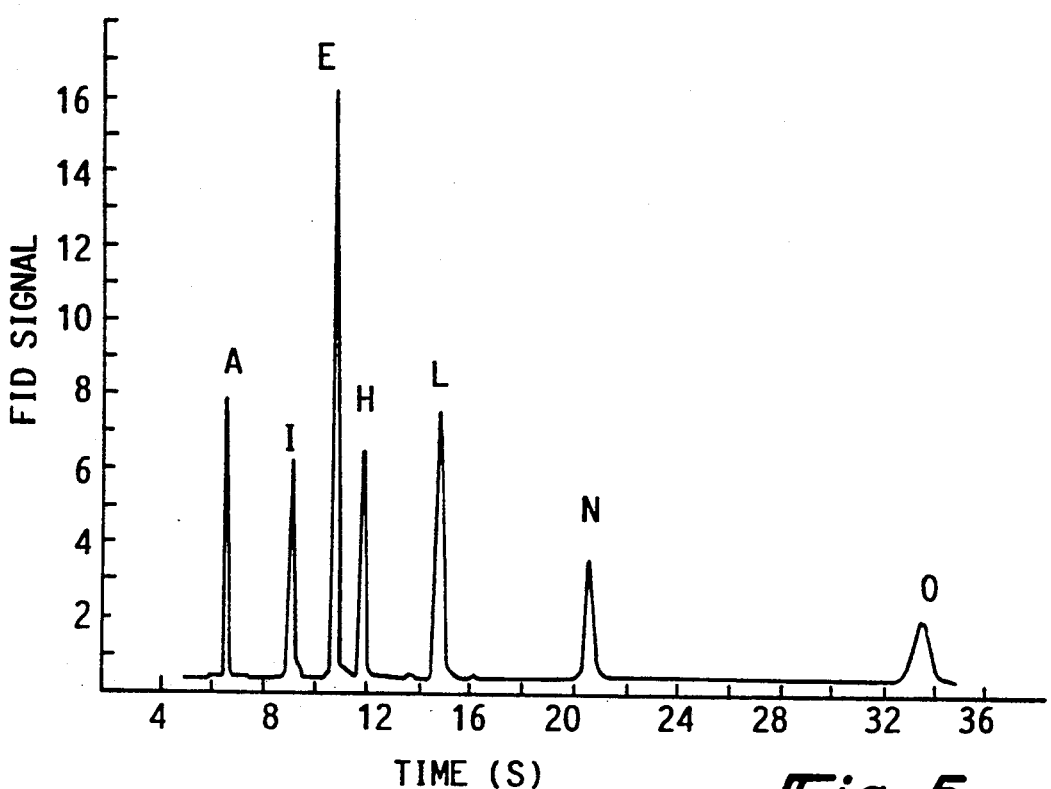
FIG. 5 is a chromatogram showing the components eluted from a first tandem column combination from the system of FIG. 1 with column switching.
Figure 6:
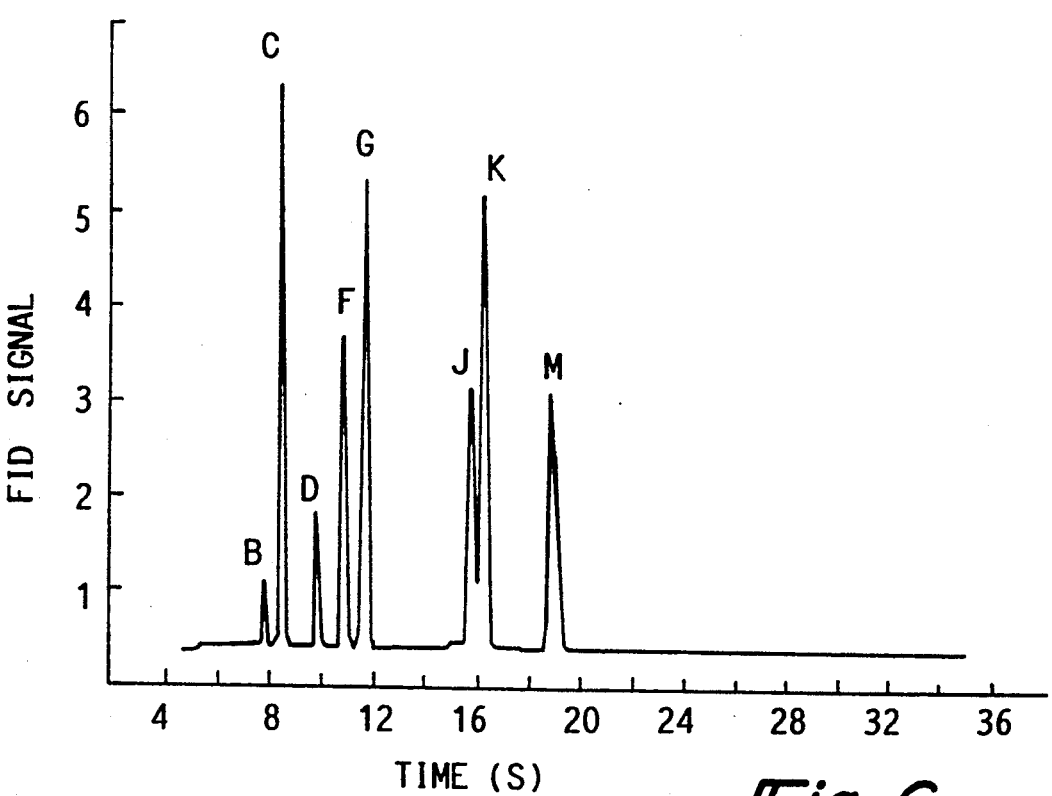
FIG. 6 is a chromatogram of a second tandem column combination from the system of FIG. 1 with column switching.

FIG. 5 is a chromatogram provided by FID 28 when column switching occurs as components A through 0 elute from column 14. In this case, the combination groups B-C-D-G, F-K, and J-M were switched from column 14 to column 22 where they are separated, whereas the other components were directed through the tandem combination of columns 14 and 24 where they produce distinct peaks A,I,E,H,L,N, and 0. FIG. 6 represents a chromatogram from FID 26 where the switched components B,C,D,G,F,K,J, and M elute. It should be noted with this switching arrangement, each of the components provide distinct peaks.

Figure 7:
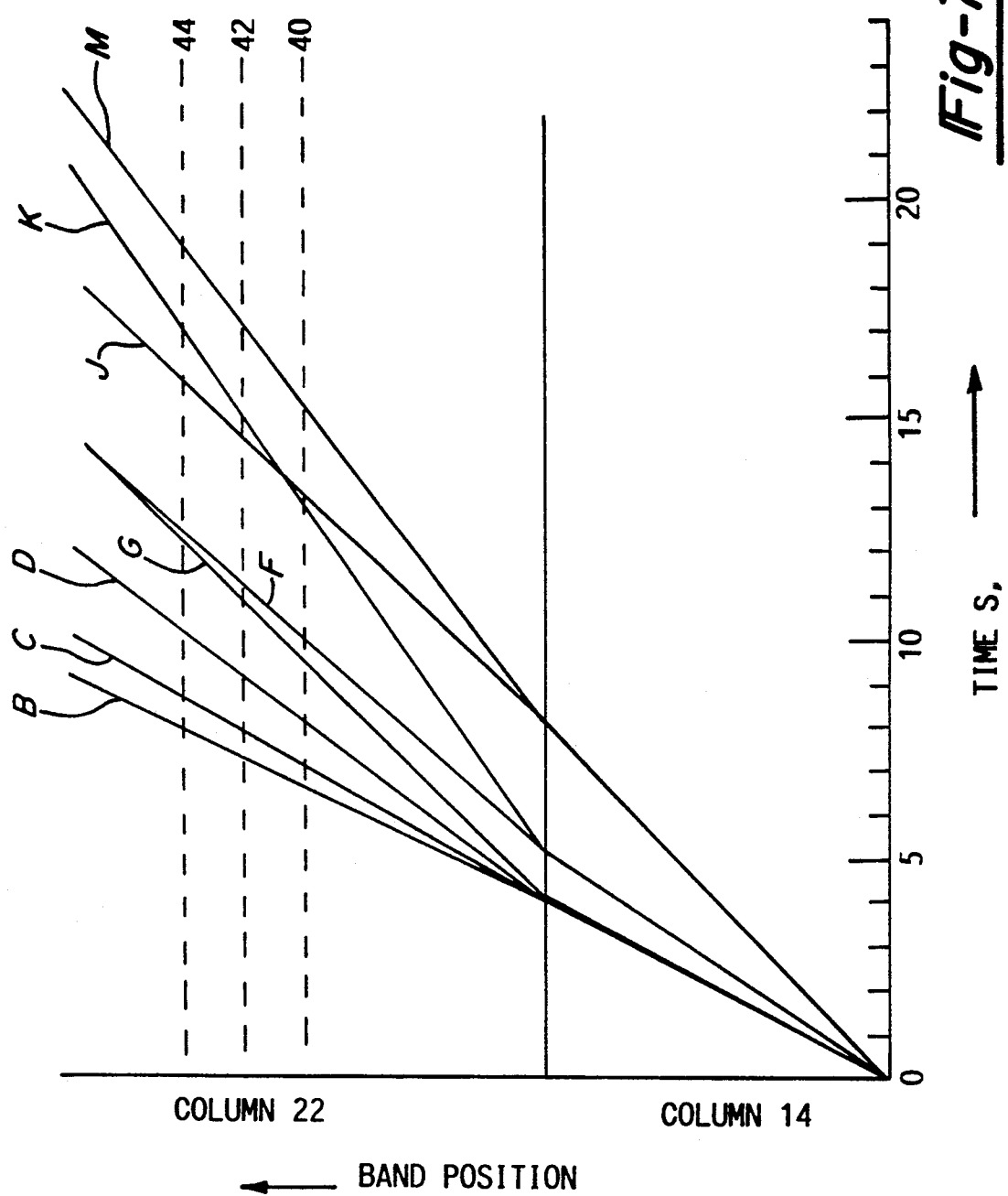
FIG. 7 is a graph showing the position of components of an actual analyte mixture on the columns of the system of FIG. 1 with respect to time.

As shown in FIG. 6, it is noted that components J and K are not completely separated on the tandem combination of columns 14 and 22. This is not because of chemical similarities but because of chance overlap of compounds of different polarity types. Note that these two compounds were introduced into column 22 at different times since they are from different switched groups eluting from column 14. The fact that they elute from column 22 at nearly the same time indicates that they must be moving through the column at different average velocities. This behavior is illustrated in FIG. 7 which is a plot of sample position versus time similar to that shown in FIG. 2, but for the components of the complex mixture which were switched into column 22 as described above. The solid horizontal line near the center of FIG. 7 corresponds to the position of the switching network of FIG. 1. Like FIG. 2, the portion below the solid line relates to flow through column 14 whereas the portion above the line relates to flow through column 22. The three broken horizontal lines 40, 42, and 44 in the upper portion of the Figure correspond to three possible effective lengths for column 22. The letters at the top of the Figure correspond to the compounds that were switched.

Note that in the lower portion of FIG. 7, the three plots correspond to the three switch groups which are the components which were not resolved in this analysis time on column 14 and would not be adequately resolved if the separation were to continue on column 24 which has selectivity characteristics consistent with that of column 14. Each of these three groups represents separate inlet "plugs" injected at different times into column 22. Thus, if any components from the different groups are found to overlap at the outlet of column 22, these components must have been traveling at different velocities, and thus their overlap is coincidental rather than caused by very similar chemical properties of the components. The plots in the upper portion of FIG. 7 show how the compounds in the three groups are separated easily on the polar column 22. The elution order B-C-D-G for the first group to enter column 22 represents increasing interaction with the stationary phase and thus increasing compound polarity with respect to the particular polar stationary phase used. The same is true for the elution orders F-K and J-M for the other two groups.

Figure 9:
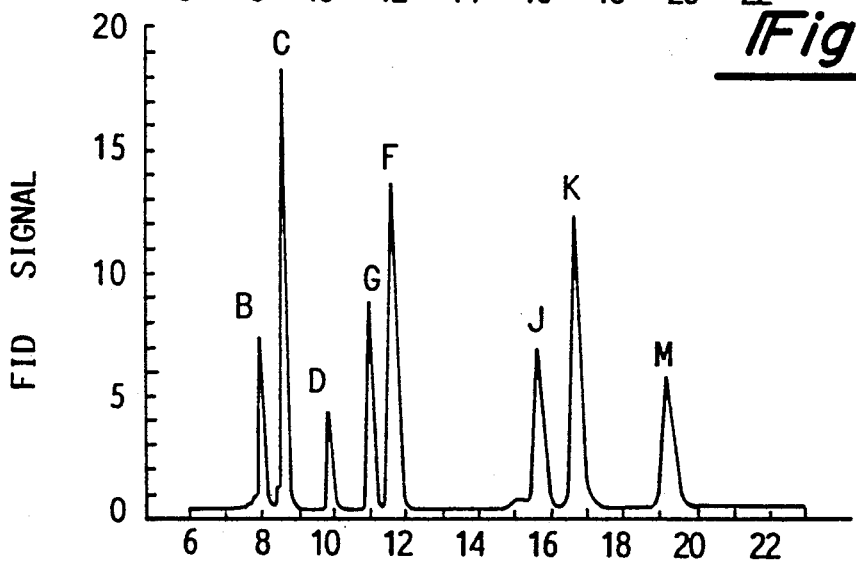

All the lines representing the compounds from a given group must diverge in column 22 in order to obtain separation. The lines for compounds G and F converge and those for J and K converge, cross, and then diverge, reflecting a considerably greater velocity for component J relative to component K. These pairs of components could overlap during elution from column 22, depending on the effective lengths of the column as designated by the three broken lines. For the shortest effective column length indicated by broken line 40 as shown in chromatogram FIG. 8, G elutes before F. Also K elutes just before J, and some overlap is present. For the intermediate effective column length, designated by the broken line 42 and as shown in chromatogram FIG. 9, G still elutes before F but their separation is significantly smaller. However, now J elutes before K and their separation is adequate. For the longest effective column length designated by broken line 44, as shown in chromatograph FIG. 10, components F and G elute very close together and J and K are very well separated. FIG. 9 represents an optimized effective length for column 22 since each component is well separated enabling quantitative evaluation of each.

As discussed, the broken lines of FIG. 7 designate different effective column lengths. There are various techniques for changing the total time that components take to travel through a column aside from changing its physical length. One approach is to change the temperature of the columns or to change the pressure and hence the velocity of the carrier gas flowing through the column. Thus, the broken lines in FIG. 7 can be thought of as representing different pressure differentials across column 22 having a constant length which are at their lowest level at broken line 44 (representing a long effective length) and at their largest level at broken line 40 (representing a short effective length). GC system 10, shown in FIG. 1, provides means for adjusting the pressure differential across the columns through the selection of restrictors 34 and 36 or by changing the carrier gas pressure at valves 30 and 32 and thus the optimal effective length can be chosen.

Figure 10:
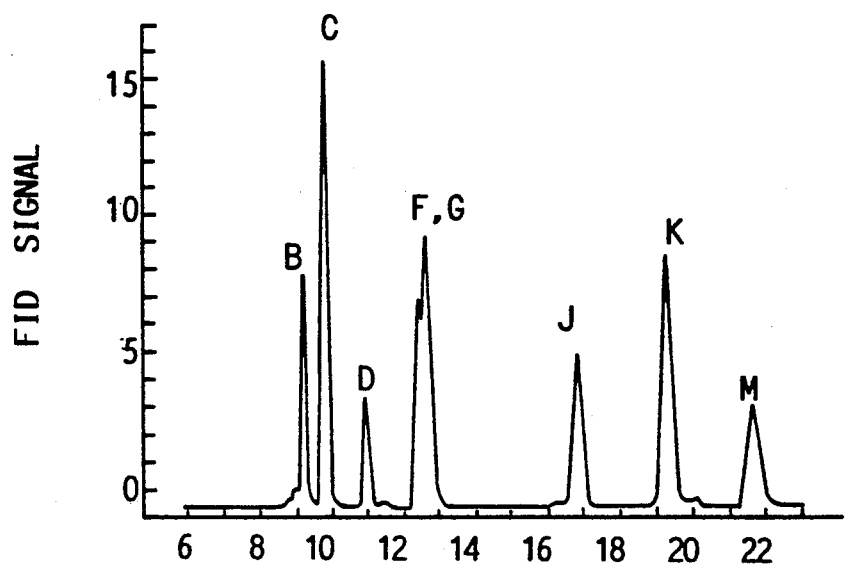
FIGS. 8 through 10 are representative chromatograms showing differences in output based on different effective lengths for one of the columns of a tandem column combination.
Figure 8:
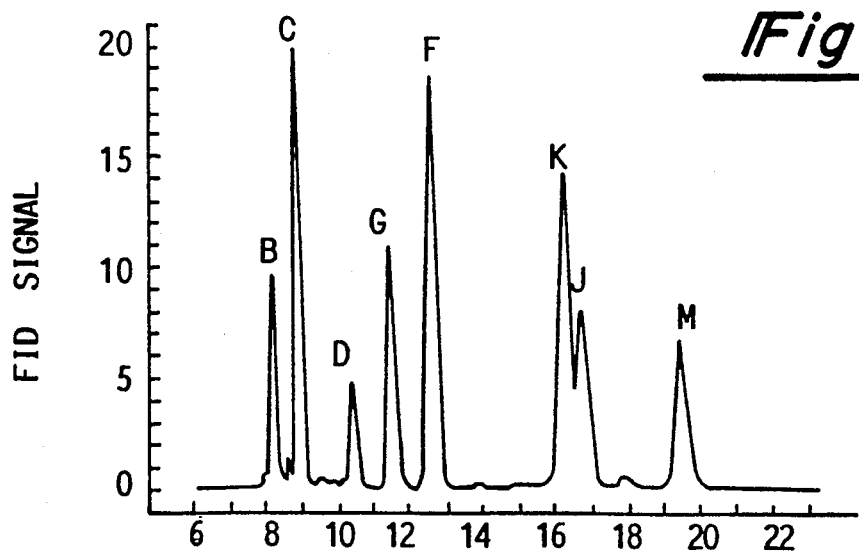

As mentioned, FIGS. 8, 9, and 10 are chromatograms taken from FIG. 6 at three different effective lengths for column 22 designated by broken lines 40, 42 and 44, respectively. For these chromatograms, the inlet pressure to column 14 is assumed to be maintained at a constant pressure above atmospheric and the outlet of columns 22 and 24 through FIDs 26 and 28 vent to atmosphere. Changing the switching pressure using the controllable source of carrier gas comprising valve 30 and 32 or restrictor 34 and 36 causes pressure drops across both columns to be changed. If the switching pressure is increased while restrictors 34 and 36 are constant, the average flow velocity in column 14 is decreased and the average flow of velocity in columns 22 or 24 is increased which increases the time that each compound spends in the column 14 and decreases the time that each compound spends in columns 22 or 24. This results in column 14 having more influence and columns 22 and 24 having less influence on the separation. An increase in the switching pressure shifts the solid horizontal line in FIG. 7 upward whereas a decrease in the switching pressure shifts the line downward. The result is similar to changing the actual lengths of the columns, but it is much simpler to change the switching pressure to change the effective lengths of the column, and thus their influence on separation. This process of providing optimal effective column lengths is referred to as "pressure control tuning."

If all components of the mixture were transferred from column 14 to column 22, the use of pressure control tuning would be much less effective because of the large number of components. By pre-selecting the components transferred to column 22, the number of potential overlapping peaks is greatly reduced with the result that the use of pressure tuning is much more effective.

For the column 14-22 tandem configuration, the most likely coincidental overlap occurs for the most polar (i.e. the most retained) component from one group directed into column 22 and the least polar (i.e. least retained) component from the next group to be switched. Adjusting the switching pressure to separate these components is straightforward since the pressure tuning adjustment will not cause changes in elution order for the components within each of the switched groups.

An important feature of GC system 10 is the fact that changing the switching pressure does not result in a significant change in the relative retention times of the various components which are separated on the tandem combination of columns 14 and 24. This is because columns 14 and 24 use the same or very similar stationary phases. Thus, as the switching pressure is changed in order to tune the selectivity of the tandem combination of columns 14 and 22, the selectivity of the tandem combination of columns 14 and 24 is relatively unaltered. This greatly simplifies the tuning process. If however, columns 14 and 24 are of different selectivities, additional selectivity tuning can be achieved since changing the switching pressure will potentially change elution order from both tandem column combinations.

The length of column 14 relative to the other two column segments can also be tuned to improve the overall separation. If column 14 is made longer, the initial separation is more complete and fewer components will need to be transferred to column 22. This reduces the work load for column 22. However, if column 14 is made longer, both columns 22 and 24 must be made shorter if the total analysis time is to be kept constant. This reduces the resolving power of columns 22 and 24. For every sample mixture, there will be an optimal length ratio for the tandem column combinations.

As mentioned previously, other approaches to tuning the selectivity of the tandem column combinations can also be used. Any change in the operating conditions of the system which causes a differential change in retention time, will change the effective lengths of the columns and can be used to tune the selectivity of the tandem combinations. These changes can also involve changes in column temperature or actual lengths of the columns.

Figure 11:
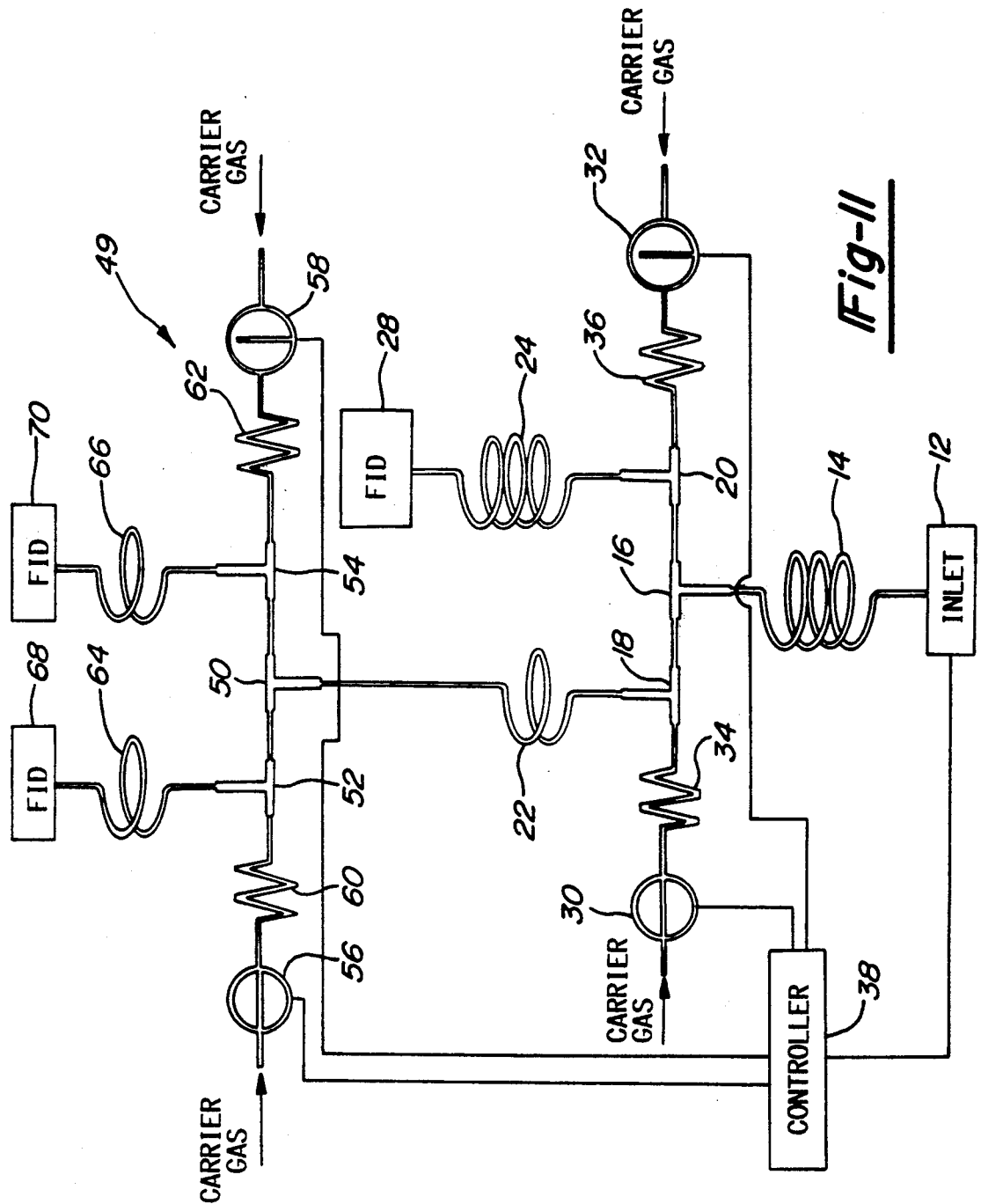
FIG. 11 is a diagrammatic view of a gas chromatography system in accordance with a second embodiment of this invention employing series coupled tandem column ensembles.

While the three columns 14, 22, and 24 shown in FIG. 1 are shown as single columns, a series-coupled tandem combination can be used to replace any of these columns. Additional bifurcation can occur at the outlet ends of either columns 22 or 24, or both, thus providing additional selectivity control. Such a system is diagrammatically illustrated in FIG. 11 and is designated as GC system 49. This figure can be thought of as including the same elements the system of FIG. 1, but FID 26 is replaced by another tandem column combination. Since the elements of the lower half of FIG. 11 are identical to those shown in FIG. 1, they are identified by like reference numbers. GC system 49 further includes additional Tee-fittings 50, 52 and 54, connected to a pair of valves 56 and 58 through pneumatic flow restrictors 60 and 62, which elements combine to provide a second switching network. Additional analytical columns 64 and 66 are provided having different selectivities. Both columns 64 and 66 could be connected to a single detector, although a pair of separate and distinct FIDs 68 and 70 are shown.

Chromatography system 49 shown in FIG. 11 includes three detectors and two switching networks. Column 22 of the first figure has essentially been supplemented with an additional segment 66 having the same selectivity. Column 64 has a different selectivity than either columns 14 or 22. Column 64 could be a polar column which shows high polarity for a different set of compounds than that of column 22. Groups of compounds which are not adequately separated on the tandem combination 14 and 22 are switched to column 64 where they are separated. The tandem combination of columns 22 and 64 can be tuned by adjusting the switching pressure applied through valve 58 and restrictor 62. If the columns 22 and 66 have the same or similar selectivities, changes in switching pressure will not significantly affect the pattern of the elution peaks from that combination. Thus, the tandem combination of column 22 and 64 can be independently tuned. Note, however, that tuning of the tandem combination of columns 22 and 64 can "untune" the upstream combination of columns 14 and 22, unless other pressures in the system are adjusted. Restrictors 34, 36, 60 and 62 would be selected to provide a pressure differential across each column to provide forward sample flow.

It is to be understood that the invention is not limited to the exact construction or method illustrated and described above, but that various changes and modifications may be made without departing from the spirit and scope of the invention as defined in the following claims.

We claim:

1. A gas chromatography method for separating components of an analyte mixture comprising the steps of:
   providing first, second, and third chromatography columns each having inlets and outlets for causing separation of the components of said analyte mixture,
   injecting the analyte into the first column thereby causing at least partial separation of the analyte mixture,
   applying a carrier gas at the inlets of the second and third columns such that the pressure of said carrier gas is greater at the second column inlet causing at least some components of the analyte flow into the third column and thereafter causing the pressure of said carrier gas to be greater at the third column inlet causing other components of the analyte to flow into the second column, and
   providing a detector for receiving components of the analyte eluting from the second and third columns.

2. The gas chromatography method according to claim 1 further comprising the step of introducing the analyte to the first column inlet a pressure grater than atmosphere and maintaining the outlets of the second and third columns at atmospheric pressures and adjusting the pressure of the carrier gas at the inlets to the second and third columns to be at a level between the first column inlet and second and third column outlet pressures such that the relative influences on separation of the first and either of the second and third columns are adjusted to provide a desired output based on the constituents of the analyte mixture.

3. The gas chromatography method according to claim 1 wherein the first and second columns have similar selectivities such that changes in the pressure of said carrier gas at the third column inlet has little effect on the separation of components passing through the first and second columns.

4. A gas chromatography system for separating components of an analyte mixture, comprising:
   an inlet system for providing a sample of the analyte mixture entrained on a stream of a carrier gas,
   a first chromatography separation column for receiving said sample from said inlet system and for causing at least partial separation of the components,
   a second chromatography separation column for receiving at least some of said components defining a first group eluting from said first column,
   a third chromatography separation column for receiving at least some of said components defining a second group eluting from said first column,
   a switching network for receiving the sample components eluting from said first column and for selectively directing said components eluting from said first column to either said second column or said third column, said switching network including a branching connection communicating said first column with a first branch connected to said second column and a second branch connected to said third column, and first and second controllable sources of carrier gas for selectively introducing carrier gas into said first and second branches at a pressure less than the pressure of said carrier gas at said inlet system whereby said carrier gas introduced by said first controllable source causes components of said analyte to be directed through said third column and carrier gas introduced by said second controllable source caused components of said analyte to be directed through said second column, and
   detector means for sensing said components eluting from at least one of said second and third columns.

5. A gas chromatography system according to claim 4 wherein said detector means vents to atmosphere said components eluting from at least one of said second and third columns.

6. A gas chromatography system according to claim 4 wherein said first and second controllable sources of carrier gas include an on/off valve and a pneumatic flow restrictor.

7. A gas chromatography system according to claim 6 wherein said first and second controllable sources of carrier gas direct the flow of analyte components through said first and second branches without said analyte components passing through either of said first or second controllable sources of carrier gas.

8. A gas chromatography system according to claim 4 wherein said first and second columns have equivalent selectivities whereas said third column has selectivity different than said first and second columns and at least some of said components not adequately separated on said first and second columns are separated on said third column.

9. A gas chromatography system according to claim 4 further comprising a controller for controlling the injection of said analyte into said first column and controlling said first and second controllable sources of carrier gas for causing said first group of components of said analyte mixture to be directed to said second column and said second group of components of said analyte to be directed to said third column.

10. A gas chromatography system according to claim 4 further comprising a fourth chromatography separation column and a fifth chromatography separation column receiving components of said analyte eluting from said second column or said third column and having a second switching network for selectively directing components eluting from a said second or said third column to either said fourth or fifth columns.

11. A gas chromatography system according to claim 4 wherein said switching network causes said carrier gas to flow through both said second and third columns while said analyte is directed through one of said second or third columns.

12. A gas chromatography system for separating components of an analyte mixture, comprising:
   an inlet system for providing a sample of the analyte mixture entrained on a stream of a carrier gas,
   a first chromatography separation column for receiving said sample and for causing at least partial separation of the components,
   a second chromatography separation column for receiving at least some of said components defining a first group eluting from said first column,
   a third chromatography separation column for receiving at least some of said components defining a second group eluting from said first column, wherein at least one of said second or third columns has a different selectively than said first column,
   a switching network for receiving the sample components eluting from said first column and for selectively directing said components eluting from said first column to either said second column or said third column, said switching network including a branching connection communicating said first column with a first branch connected to said second column and a second branch connected to said third column, and first and second controllable sources of carrier gas each including an on/off gas valve and a flow restrictor for selectively introducing carrier gas into both said first and second branches at a pressure less than the pressure of carrier gas at said inlet system whereby carrier gas introduced by said first controllable source causes components of said analyte eluting from said first chromatography separation column to be directed through said third column and carrier gas introduced by said second controllable source causes components of said analyte eluting from said first chromatography separating column to be directed through said second column,
   detector means for sensing said components eluting from at least one of said second and third columns, and
   a controller for controlling the injection of said analyte into said first column and controlling said first and second controllable sources of carrier gas from causing some components of said analyte mixture eluting from said first chromatography separation column to be directed to said second column and other components of said mixture to be directed to said third column.

13. A gas chromatography system according to claim 12 wherein said detector means vents to atmosphere said components eluting from at least one of said second and third columns.

14. A gas chromatography system according to claim 12 wherein said first and second columns have equivalent selectivities whereas said third column has a selectivity different than said first and second columns and at least some of said components not adequately separated on said first and second columns are separated on said third column.

15. A gas chromatography system according to claim 12 further comprising a fourth chromatography separation column and a fifth chromatography separation column receiving components of said analyte eluting from said second column or said third column and having a second switching network for selectively directing components eluting from said second or said third column to either said fourth or fifth columns.

* * * * *

UNITED STATES PATENT AND TRADEMARK OFFICE
CERTIFICATE OF CORRECTION

PATENT NO. : 5,281,256
DATED : February 15, 1994
INVENTOR(S) : Richard D. Sacks, et al.

It is certified that error appears in the above-indentified patent and that said Letters Patent is hereby corrected as shown below:

Column 10, Line 36, Claim 4 delete "caused" and insert --causes--.

Column 10, Line 56, Claim 8 after "has" insert --a--.

Column 12, Line 9, Claim 12 delete "separating" and insert --separation--.

Column 9, Line 48, Claim 1 after "analyte" insert --to--.

Column 9, Line 57, Claim 2 after "inlet" insert --at--.

Column 9, Line 57, Claim 2 delete "grater" and insert --greater--.

Column 9, Line 64, Claim 2 after "columns" delete "are" and insert --can be--.

Signed and Sealed this

Twenty-sixth Day of July, 1994

Attest:

BRUCE LEHMAN

*Attesting Officer*  *Commissioner of Patents and Trademarks*